(12) United States Patent
Singh et al.

(10) Patent No.: US 8,908,031 B2
(45) Date of Patent: Dec. 9, 2014

(54) APPARATUS AND METHOD FOR MEASURING MOISTURE CONTENT IN STEAM FLOW

(75) Inventors: Anurag Singh, Glenville, NY (US); Michael Joseph Boss, Ballston Spa, NY (US)

(73) Assignee: General Electric Company, Schenectady, NY (US)

( * ) Notice: Subject to any disclaimer, the term of this patent is extended or adjusted under 35 U.S.C. 154(b) by 439 days.

(21) Appl. No.: 13/299,455

(22) Filed: Nov. 18, 2011

(65) Prior Publication Data

US 2013/0128031 A1 May 23, 2013

(51) Int. Cl.
*H04N 7/18* (2006.01)
*G01N 21/53* (2006.01)
*F01K 7/16* (2006.01)

(52) U.S. Cl.
CPC . *G01N 21/53* (2013.01); *F01K 7/16* (2013.01)
USPC .......................................................... 348/135

(58) Field of Classification Search
USPC ........................................................... 348/135
See application file for complete search history.

(56) References Cited

U.S. PATENT DOCUMENTS

| 4,137,462 | A | | 1/1979 | Wyler |
| 5,123,277 | A | * | 6/1992 | Gray et al. ................... 73/29.01 |
| 5,380,440 | A | * | 1/1995 | Chipps .......................... 210/709 |
| 5,982,478 | A | * | 11/1999 | Ainsworth et al. ............. 356/28 |
| 7,345,280 | B2 | | 3/2008 | Mitra et al. |
| 7,381,954 | B2 | | 6/2008 | Banerjee et al. |

* cited by examiner

*Primary Examiner* — Dave Czekaj
*Assistant Examiner* — Tracy Li
(74) *Attorney, Agent, or Firm* — Hoffman Warnick LLC; Ernest G. Cusick

(57) ABSTRACT

An apparatus and method for estimating moisture content in a steam flow through a steam turbine is disclosed. At least a portion of a steam flow path through a turbine is illuminated using at least one laser assembly, and a plurality of digital images of the illuminated portion of the steam flow are obtained. The digital images are analyzed to measure an amount of light scattered in each digital image, and this analysis of each digital image is compared to estimate moisture content of the steam flow.

12 Claims, 5 Drawing Sheets

APPARATUS AND METHOD FOR MEASURING MOISTURE CONTENT IN STEAM FLOW

BACKGROUND OF THE INVENTION

The disclosure relates generally to turbomachines such as a steam turbine, and more particularly, to an apparatus and method for measuring moisture content in the steam flow through the turbomachine.

Measurement of the steam quality in a steam turbine is often desired in order to develop better models and validation techniques, conduct tests, improve calculation methods in external or internal tools, improve the turbine's performance estimation, improve turbine control and plant control (such as tuning condenser performance, heat recovery steam generator (HRSG) adjustments and gas turbine operation) and other related items which may benefit from an accurate measurement of this parameter. However, current methods of measuring the quality of steam in a steam turbine do not provide an accurate, non-invasive and/or cost effective means for measuring steam quality during normal operation of the turbine.

BRIEF DESCRIPTION OF THE INVENTION

The apparatus and methods disclosed herein disclose a solution for a non-invasive method to measure the quality of steam in a steam turbine. Specifically, at least a portion of a steam flow path through a turbine is illuminated using at least one laser assembly, and a plurality of digital images of the illuminated portion of the steam flow are obtained, e.g., at discrete time intervals. The digital images are analyzed to measure an amount of light scattered in each digital image, and this analysis of each digital image is compared to estimate moisture content of the steam flow.

A first aspect of the disclosure provides a system for estimating moisture content in a steam flow through a steam turbine, the system comprising: at least one laser assembly configured to illuminate at least a portion of the steam flow; at least one image sensor configured to obtain a plurality of digital images of the illuminated portion of the steam flow; and a computing device operatively coupled to the at least one image sensor, the computing device configured to: analyze the plurality of digital images to measure an amount of light scattered in each digital image; and compare the analysis of the plurality of digital images to estimate moisture content of the steam flow.

A second aspect of the disclosure provides a method of estimating moisture content in a steam flow through a steam turbine, the method comprising: illuminating at least a portion of the steam flow using a laser assembly; obtaining a plurality of digital images of the illuminated portion of the steam flow using at least one image sensor; analyzing the plurality of digital images to measure an amount of light scattered in each digital image; and comparing the analysis of the plurality of digital images to estimate moisture content of the steam flow.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

Figure 1:
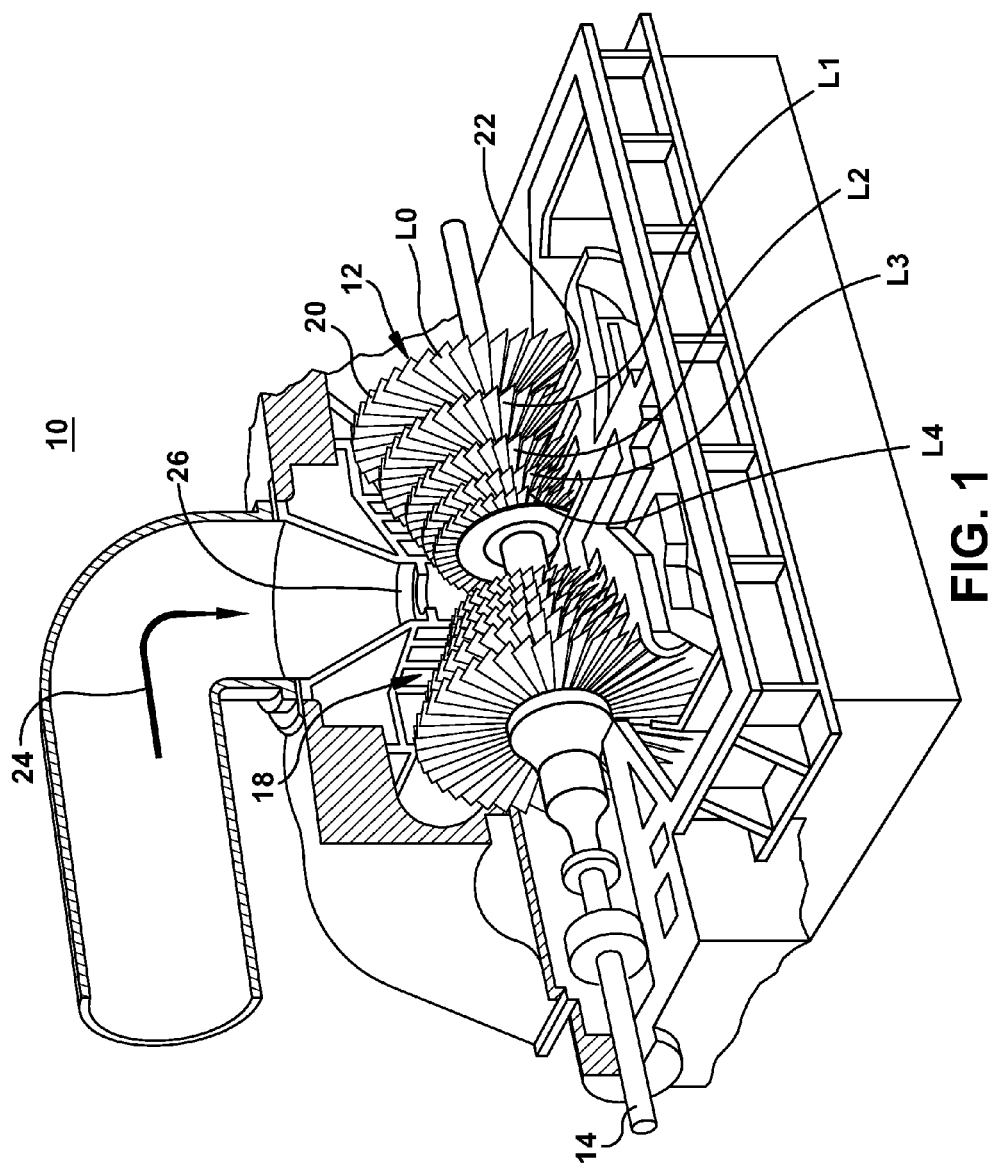
FIG. 1 shows a perspective partial cut-away illustration of a steam turbine.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

At least one embodiment of the present invention is described below in reference to its application in connection with the operation of a turbomachine. Although embodiments of the invention are illustrated relative to a turbomachine in the form of a steam turbine, it is understood that the teachings are equally applicable to other turbomachines, including but not limited to gas turbines. Further, at least one embodiment of the present invention is described below in reference to a nominal size and including a set of nominal dimensions. However, it should be apparent to those skilled in the art that the present invention is likewise applicable to any suitable turbine and/or generator. Further, it should be apparent to those skilled in the art that the present invention is likewise applicable to various scales of the nominal size and/or nominal dimensions.

Referring to the drawings, FIG. 1 shows a perspective partial cut-away illustration of a steam turbine 10. The steam turbine 10 includes a rotor 12 that includes a shaft 14 and a plurality of axially spaced rotor wheels 18. A plurality of rotating blades 20 are mechanically coupled to each rotor wheel 18. More specifically, blades 20 are arranged in rows that extend circumferentially around each rotor wheel 18. A plurality of stationary vanes 22 extend circumferentially around shaft 14 and are axially positioned between adjacent rows of blades 20. Stationary vanes 22 cooperate with blades 20 to form a turbine stage and to define a portion of a steam flow path through turbine 10.

In operation, steam 24 enters an inlet 26 of turbine 10 and is channeled through stationary vanes 22. Vanes 22 direct steam 24 downstream against blades 20. Steam 24 passes through a plurality of stages imparting a force on blades 20 causing shaft 14 to rotate. At least one end of turbine 10 may extend axially away from rotor 12 and may be attached to a load or machinery (not shown) such as, but not limited to, a generator, and/or another turbine. Accordingly, a large steam turbine unit may actually include several turbines that are all co-axially coupled to the same shaft 14. Such a unit may, for example, include a high pressure turbine coupled to an intermediate-pressure turbine, which is coupled to a low pressure turbine.

As shown in FIG. 1, turbine 10 can comprise multiple stages, for example, the five stages referred to as L0, L1, L2, L3 and L4 shown in FIG. 1. Stage L4 is the first stage and is the smallest (in a radial direction) of the five stages. Stage L3 is the second stage and is the next stage in an axial direction. Stage L2 is the third stage and is shown in the middle of the five stages. Stage L1 is the fourth and next-to-last stage. Stage L0 is the last stage and is the largest (in a radial direction). It is to be understood that five stages are shown as one example only, and a turbine can have more or less than five stages.

Before or close to start up of the turbine, there will be substantially no steam flowing through the machine. This is referred to as a "dry" or "inoperative" state. Once the turbine is up and running, as the steam moves through steam turbine 10, condensation can begin, and moisture (e.g., water, steam or a mixture of water and steam) can form. This is referred to as a "wet" or "operative" state. It is often desirable to measure how much moisture is present in the steam flow at a given time during operation of the turbine. To accomplish this, a system 100 (FIG. 2) is provided which provides a non-invasive method to accurately measure the quality of steam in a steam turbine.

Figure 2:
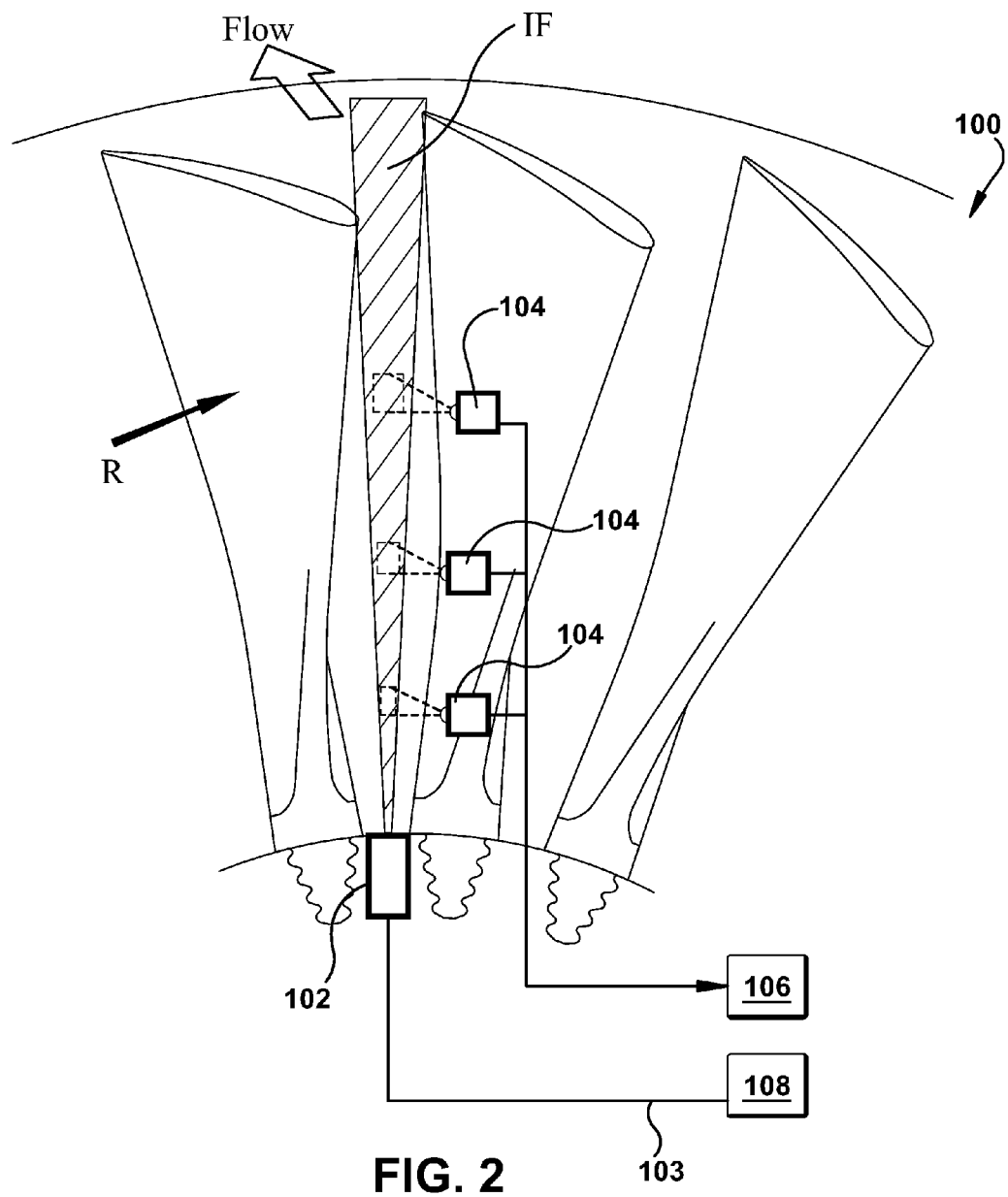
FIG. 2 shows a partial view of a steam turbine including a system for estimating moisture content in a steam flow according to a first embodiment of the invention disclosed herein.

Turning to FIG. 2, a system 100 for estimating moisture content in a steam flow through a steam turbine is shown. System 100 makes use of the techniques of time resolved digital particle image velocimetry, and the fact that light-scattering properties of steam depend, in part, on the moisture content of the steam. Specifically, wet steam will scatter more light when compared to dry steam. Therefore, embodiments of the invention disclosed herein illuminate steam flow using a laser, then takes digital images of the illuminated steam flow. The digital images can be analyzed and compared to estimate the moisture quality of the steam flow. Using the apparatus and methods disclosed herein, the moisture content of the steam flow is analyzed without interrupting the natural steam flow path, i.e., nothing is added to the steam flow, as in previously known methods of monitoring moisture content.

System 100 includes at least one laser assembly 102 configured to illuminate at least a portion of the steam flow path through the steam turbine. Laser assembly 102 can comprise any components capable of illuminate the steam flow in a turbine, for example, a fiber optic cable 103 and a cylindrical and convex lens assembly, where the fiber optic cable 103 could be accessible from outside the turbine (for example, by connecting to a laser source 108, discussed herein) so that a laser beam could be directed to illuminate the steam flow. One or more laser assemblies 102 can be provided and positioned as desired in order to illuminate a portion of the steam flow, for example, one laser assembly 102 could be included at one end of the steam path and a second at the other end of the steam path, such that the entire steam path could be illuminated by the two laser assemblies. For example, as shown in FIG. 2, one laser assembly 102 can be positioned on a rotating component of the steam turbine, whereas in FIG. 3, two laser assemblies 102 are used, for example, one laser assembly 102 is positioned on the rotating component, while a second laser assembly 102 is positioned on a stationary component.

Figure 3:
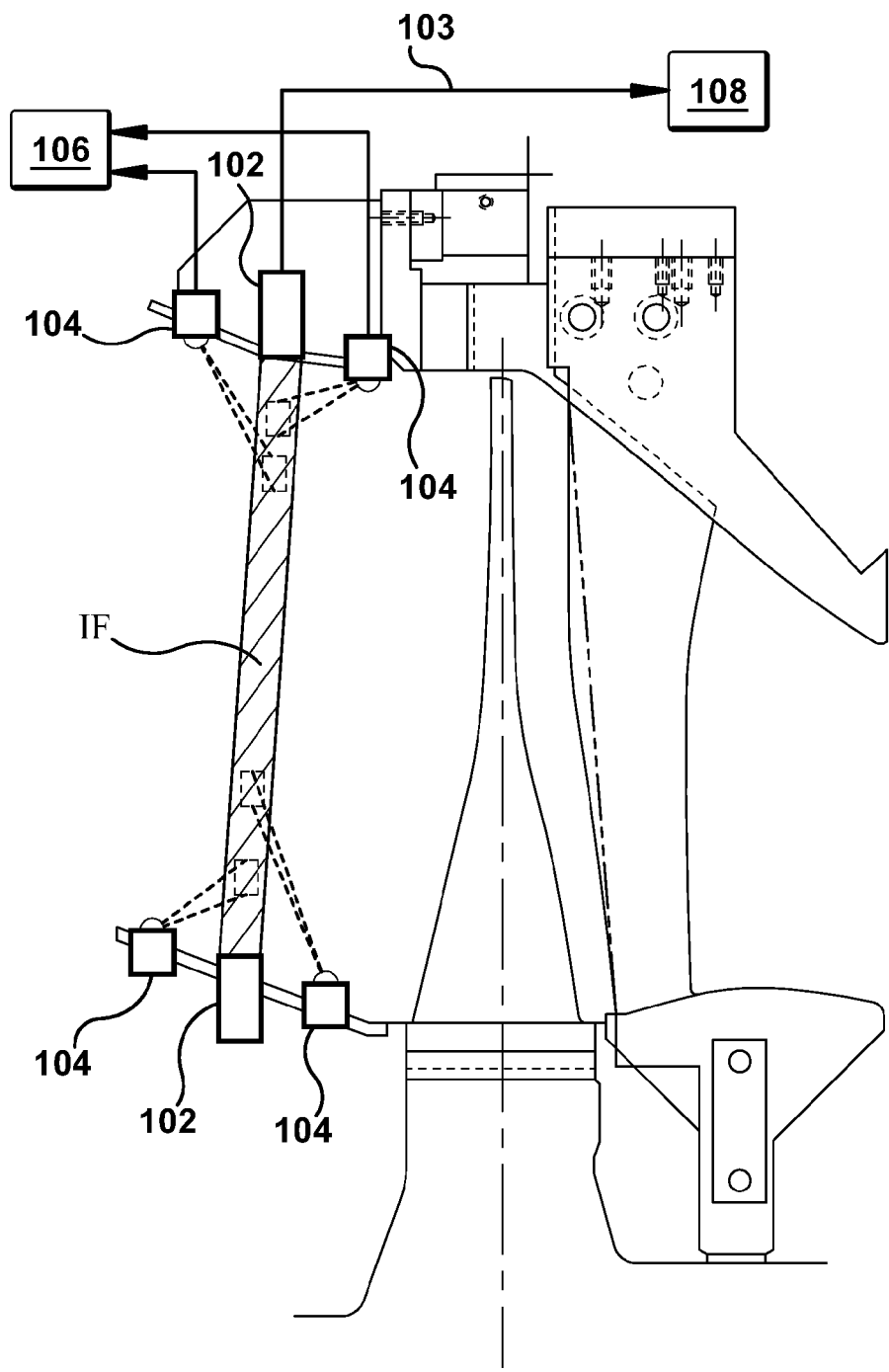
FIG. 3 shows a partial view of a steam turbine including a system for estimating moisture content in a steam flow according to a second embodiment of the invention disclosed herein.

As shown in FIGS. 2 and 3, regardless of positioning, laser assembly 102 is configured to illuminate a portion of the steam flow through the steam turbine. For example, laser assembly 102 emits a laser beam that provides a sheet of laser light, illustrated in FIGS. 2 and 3 by the shading, IF, that illuminates a portion of the steam flow. This illuminated flow, IF, can be any portion of the steam flow through the steam turbine that a user desires to measure.

System 100 further includes at least one image sensor 104 configured to obtain a plurality of digital images of the illuminated portion of the steam flow, IF, at discrete time intervals. Any number of images taken over a period of time can be used, for example, 1000 images per second, 1000 images per 30 seconds, 600 images per second, etc. Image sensor 104 can comprise any now known or later developed sensor capable of capturing a digital image. For example, the sensor can comprise, an image sensor produced by a complementary metal-oxide-semiconductor (CMOS) process (CMOS sensor), i.e., an active-pixel image sensor, or a charge-coupled device (CCD) image sensor. Image sensors 104 can be positioned as desired, e.g., on a rotating component or a stationary component of the steam turbine, and any number of sensors 104 can be used. For example, as shown in FIG. 2, three image sensors 104 can be used, each positioned on a rotating blade. In this example, image sensors 104 are positioned approximately perpendicular to the laser beam illuminating the illuminated flow, and the field of view (illustrated by the dotted lines in FIG. 2) of each image sensor 104 is within the illuminated flow, IF. In another example, shown in FIG. 3, image sensors 104 can be positioned substantially parallel to the illuminated flow, IF, for example, on the stationary component and/or on the rotating component.

Regardless of the number or placement of image sensors 104, image sensors 104 are configured to take a digital image of a portion of the illuminated flow. Therefore, image sensors 104 can be positioned in any way such that the field of view of the image sensor is within the illuminated flow. Specifically, image sensors 104 can be positioned such that a lens of an image sensor 104 is focused precisely on a desired location in the illuminated flow field.

Figure 4:
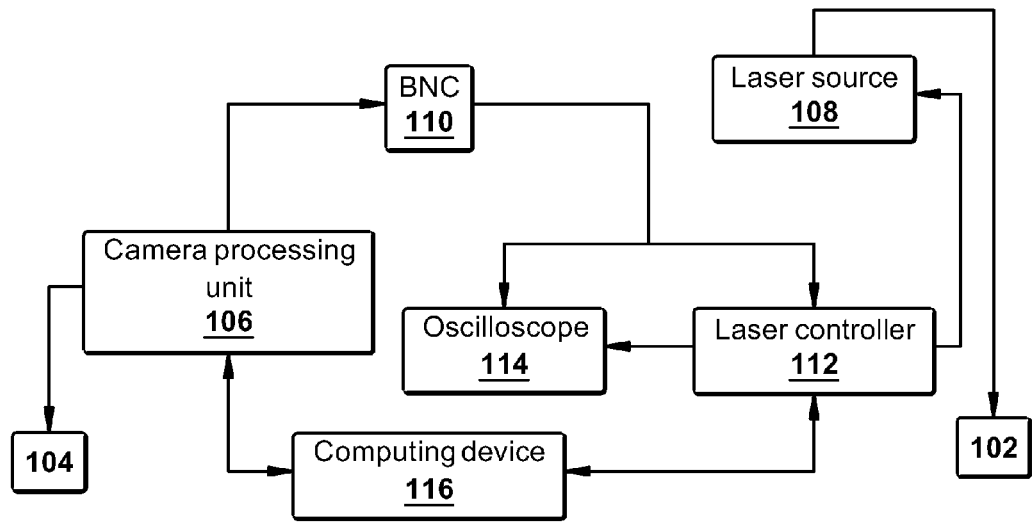
FIG. 4 shows an illustrative schematic of external connections at least partially outside a steam turbine that connect to the systems disclosed herein.

As shown in FIGS. 2 and 3, system 100 further includes external connections to provide the laser beam and to process the digital images taken by the image sensors 104. FIG. 4 shows an illustrative arrangement of external connections at least partially outside a steam turbine that connect to system 100. For example, a camera processing unit 106 can be provided, operatively coupled to at least one image sensor 104. Camera processing unit 106 is configured to process the plurality of digital images taken by image sensors 104. In addition, at least one laser source 108 (e.g., a high speed laser) can be operatively connected (e.g., through optical cable 103 shown in FIG. 3) to at least one laser assembly 102. Laser source 108 and camera processing unit 106 can be synched together to fire the laser and to capture an image using a timing and trigger box 110, for example, a BNC connector (Bayonet Neill-Concelman). As understood by one of skill in the art, the external connections can further include a laser controller 112 and oscilloscope 114 coupled to laser source 108 and BNC connector 110 to sync the timing of the laser and the digital image.

At least one computing device 116 is operatively connected to image sensors 104 (through camera processing unit 106 or directly connected) to further process the digital images taken by the image sensors 104. Computing device 116 can also be operatively connected to laser assembly 102 (through optical cable 103 and laser source 108/laser controller 112). Images taken by image sensors 104 can be analyzed by camera processing unit 106 or computing device 116. Either way, the digital images are analyzed to measure an amount of light scattered in each digital image. Then, the analyzed images are compared to estimate moisture content of the steam flow, as discussed herein.

Figure 5:
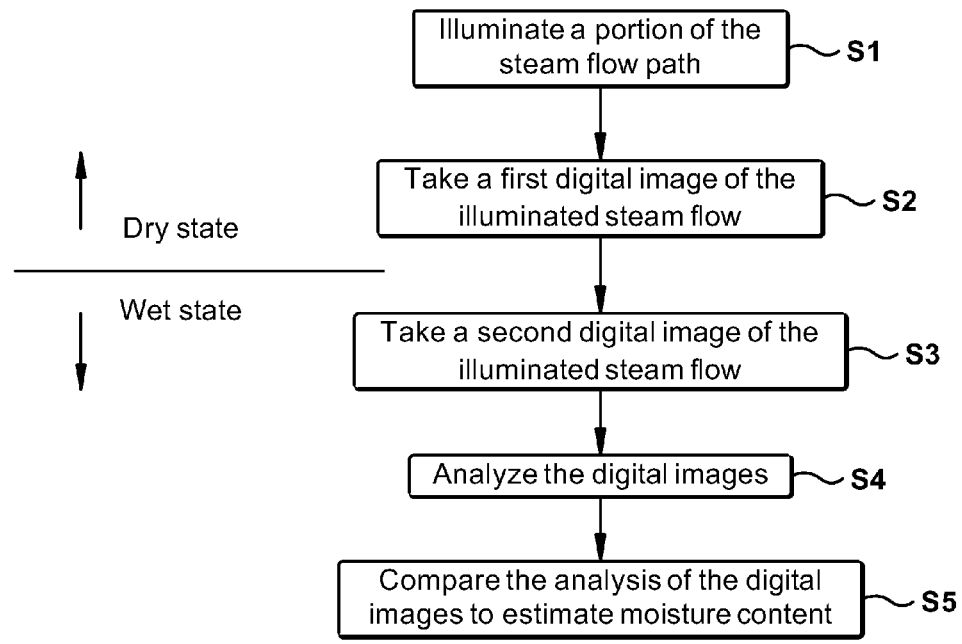
FIG. 5 shows a flow chart illustrating a method for estimating moisture content in a steam flow according to embodiments of the invention disclosed herein.

A method for estimating moisture content in a steam flow using system 100 is shown in FIG. 5. First, as shown in step S1, at least one laser assembly is used to illuminate at least a portion of the steam flow through a turbine. Next, as shown in steps S2 and S3, a plurality of digital images of the illuminated portion of the steam flow are obtained at discrete time intervals using at least one image sensor. In one embodiment, a first digital image is taken at a first point in time when the steam turbine is in a dry state, and a second digital image is taken at a later, second point in time, when the steam turbine is in a wet state. Although, it is understood that the plurality of images can all be taken in a dry state, or all in a wet state, or any combination thereof. Next, as shown in step S4, the digital images are analyzed, for example, to determine an amount of light scattered as the laser beam illuminates the steam flow. In step S5, the results of the analysis of the digital images are compared to estimate the moisture content of the steam flow. In one embodiment, a second digital image taken in the wet state, is compared to a first digital image taken in the dry state, to estimate moisture content of the steam flow at the second point in time. In this way, the first digital image taken during the dry state is used as a calibration image (i.e., an image of a flow with a known moisture content), and all subsequent digital images can be compared against the calibration image to estimate moisture content at those subsequent times. In another embodiment, a plurality of images are all taken in a wet state, and instead of comparing against a dry, calibration image, the plurality of images are compared against each other to determine how the moisture content changed over time.

It is also understood that rather than a first image taken by an image sensor as a calibration image, the calibration image could be obtained from a lab test or other source. In addition, a calibration image could be an instantaneous image or an averaged image for which the moisture content is known (e.g., 100% dry image or 100% wet image or something in between with a known moisture content). Regardless of how a calibration or base image with a known moisture content is obtained, it can be compared to a single instantaneous image or an averaged image over a period of time. The comparisons can be used to study and generate a wide range of statistics as well as give more insight about the moisture content of the flow.

Although for ease of illustration, the method discussed above is described in connection with taking one calibration digital image and one digital image at a later point in time, it is understood that any number of images can be taken. For example, a plurality of calibration images can be taken in a dry state, and the analysis (e.g., intensity distribution) for each digital image can be averaged together to determine an average amount of light scattered in each digital image. Similarly, a plurality of digital images can be taken in a wet state. For example, images can be taken near continuously, or at set intervals. The plurality of wet digital images can be analyzed and the analysis (e.g., intensity distribution) for each digital image can be averaged together to determine an average amount of light scattered. In this way, a set of digital images taken in a given period of time can be averaged, and the average can be compared with the calibration image to estimate the moisture content of the steam flow during the given period of time.

Figure 6:
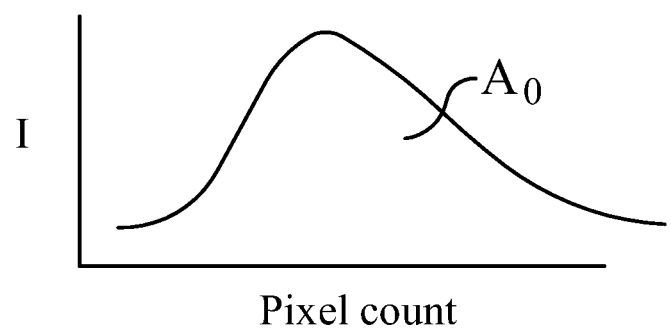
FIG. 6 shows a typical plot of intensity versus pixel count of an analysis of a digital image taken in a dry state according to embodiments of the invention disclosed herein.
Figure 7:
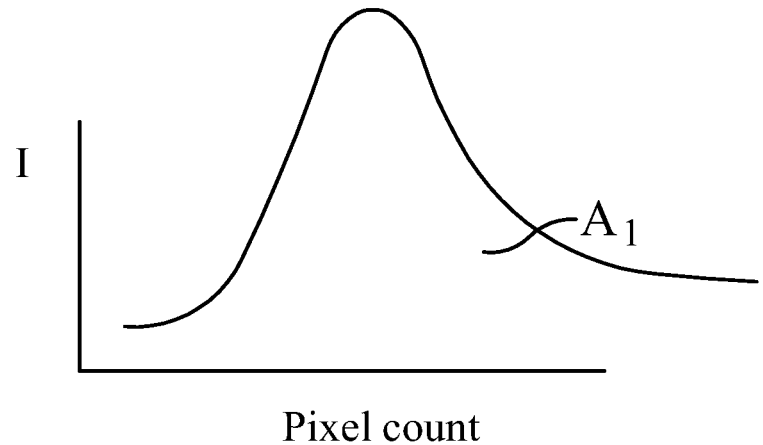
FIG. 7 shows a typical plot of intensity versus pixel count of an analysis of a digital image taken in a wet state according to embodiments of the invention disclosed herein.

The digital images can be analyzed and compared in any way to estimate the moisture content. In one embodiment, each digital image is analyzed to determine an intensity distribution, and the intensity distributions for each digital image are compared. The intensity distribution can be expressed as a plot of intensity versus pixel count, as shown in FIGS. 6 and 7. As known in the art, a digital image sensor is divided into pixels and each pixel essentially corresponds to an integer number representing the level of light it registered. Depending on the sensitivity of the pixels/image sensors (e.g., bit width), this number could range from 0 to $2^n$, where n is the bit width. For example, for an 8-bit pixel, this number is typically between 0-255. Therefore, depending on the image sensor used, the intensity will be an integer number. This number can be plotted against the pixel count and thus a distribution profile over the entire sensor can be plotted. The area under the curve represents the total light sensed by the image sensor.

FIG. 6 shows a typical intensity distribution for a dry state, showing a relatively flat curve (with area $A_0$ under the curve) because there is generally less variation of intensity across pixels when there is less moisture present. In contrast, FIG. 7 shows a typical intensity distribution in a wet state, showing a relatively higher curve (with area $A_1$ under the curve) because there is generally more variation of intensity across pixels when there is more moisture present. This is because wet steam refracts more light than dry steam, therefore there will be a higher refraction of light when there is more moisture in the steam flow. Because the steam flow has been illuminated by the laser beam, the digital image will show the amount of laser light refracted by the moisture present in the steam flow.

Various algorithms can be used to compare the amount of light refracted in each digital image. In one embodiment, using the example shown in FIGS. 6 and 7, the following algorithm can be used, which focuses on the difference, $\Delta_{Area}$, between the two areas, $A_0$ and $A_1$, to measure the quality of steam, Q:

$$Q = \Delta_{Area}/A_0 = ((A_1 - A_0)/A_0) \times 100\%$$

It is understood that this algorithm and approach for comparing is in no way limiting and there are any number of ways to analyze and compare the image data. For example, the intensities could be normalized and then compared, thus creating "moisture maps" or tables that can be easily read for a given intensity ratio. Essentially, once the intensity data is obtained as discussed herein, any number of statistical analysis can be done to gain insight into the flow field. For example, averaging them over certain period of time, e.g., 1000 images, 100 images, etc., taken over 1 min, 5 min, 2 sec, etc. (any combination is possible), appropriate averaging frequency can be determined to properly analyze the data. Additionally sections of the images can also be correlated instead of the entire image.

It is also understand that the sections of the turbine shown herein are only provided as examples of how system 100 could be positioned and used within a steam turbine. For example, the blades shown in FIGS. 2 and 3 could comprise rotating blades (with rotation illustrated by arrow, R, in FIG. 2), or can comprise stationary nozzles. FIGS. 2 and 3 use steam flow through rotating blades to illustrate system 100, but it is understood that system 100 can be used to estimate moisture at any point in or around a steam turbine. Essentially, wherever steam flow exists, a light source, e.g., a laser, can be used to illuminate the flow, and digital images can be taken of that illuminated flow, and those images can be analyzed to estimate the moisture content.

Computing device 116 can comprise one or more general purpose computing articles of manufacture capable of executing program code installed thereon, for example program code configured to analyze and compare the digital images as discussed herein. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the program code can be embodied as any combination of system software and/or application software.

Further, program code discussed herein can be implemented using a module or set of modules. As used herein, the term "component" means any configuration of hardware, with or without software, which implements the functionality described in conjunction therewith using any solution, while the term "module" means program code that enables a computing device 116 to implement the actions described in conjunction therewith using any solution. When fixed in memory or storage unit of a computing device 116 that includes a processing unit, a module is a substantial portion of a component that implements the actions. Regardless, it is understood that two or more components, modules, and/or systems may share some/all of their respective hardware and/or software. Further, it is understood that some of the functionality discussed herein may not be implemented or additional functionality may be included as part of computing device 116.

When computing device 116 comprises multiple computing devices, each computing device can have only a portion of program fixed thereon (e.g., one or more modules). However, it is understood that computing device 116 and program code discussed herein are only representative of various possible equivalent computer systems that may perform a process described herein. To this extent, in other embodiments, the functionality provided by computing device 116 and program code discussed herein can be at least partially implemented by one or more computing devices that include any combination of general and/or specific purpose hardware with or without program code, including but not limited to a handheld measuring device for stator-to-rotor clearance. In each embodiment, the hardware and program code, if included, can be created using standard engineering and programming techniques, respectively.

When computing device 116 includes multiple computing devices, the computing devices can communicate over any type of communications link. Further, while performing a process described herein, computing device 116 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As previously mentioned and discussed further herein, the apparatus and methods disclosed herein have the technical effect of enabling an estimation of moisture content of a steam flow. Using a laser assembly 102 to illuminate a steam flow path in a steam turbine, digital images are taken using at least one image sensor 104. The digital images are then compared to estimate the moisture content of a steam flow at a given time.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It is further understood that the terms "front" and "back" are not intended to be limiting and are intended to be interchangeable where appropriate.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for estimating moisture content in a steam flow through a steam turbine, the system comprising:
   at least one laser assembly configured to illuminate at least a portion of the steam flow;
   at least one image sensor configured to obtain a plurality of digital images of the illuminated portion of the steam flow; and
   a computing device operatively coupled to the at least one image sensor, the computing device configured to:
      analyze the plurality of digital images to measure an amount of light that is scattered including scattering at least by the moisture content in the steam flow in each digital image; and
      compare the analysis of the plurality of digital images to estimate moisture content of the steam flow,
      wherein the analyzing includes analyzing a set of digital images taken over a period of time and averaging the analysis of each digital image together to determine an averaged amount of light scattered; and wherein the comparing includes comparing the averaged analysis of each digital image to estimate moisture content of the steam flow during the period of time.

2. The system of claim 1, wherein the at least one laser assembly includes a fiber optic cable and a lens assembly.

3. The system of claim 1, wherein the at least one image sensor comprises a complementary metal-oxide-semiconductor (CMOS) sensor or a charge-coupled device (CCD) image sensor.

4. The system of claim 1, wherein a first digital image is taken at a first point in time when the steam turbine is in a dry state, and a second digital image is taken at a later, second point in time, and the second image is compared to the first digital image to estimate moisture content of the steam flow at the second point in time.

5. The system of claim 1, wherein the at least one image sensor is positioned on a rotating component or a stationary component of the steam turbine.

6. The system of claim 1, wherein the analyzing includes analyzing each digital image to determine an intensity distribution; and the comparing includes comparing the intensity distributions for each digital image.

7. A method of estimating moisture content in a steam flow through a steam turbine, the method comprising:
   illuminating at least a portion of the steam flow using a laser assembly;
   obtaining a plurality of digital images of the illuminated portion of the steam flow using at least one image sensor;

analyzing the plurality of digital images to measure an amount of light that is scattered including scattering at least by the moisture content in the steam flow in each digital image; and comparing the analysis of the plurality of digital images to estimate moisture content of the steam flow, wherein the analyzing includes analyzing a set of digital images taken over a period of time and averaging the analysis of each digital image together to determine an averaged amount of light scattered; and wherein the comparing includes comparing the averaged analysis of each digital image to estimate moisture content of the steam flow during the period of time.

8. The method of claim 7, wherein the at least one laser assembly includes a fiber optic cable and a lens assembly.

9. The method of claim 7, wherein the at least one image sensor comprises a complementary metal-oxide-semiconductor (CMOS) sensor or a charge-coupled device (CCD) image sensor.

10. The method of claim 7, wherein a first digital image is taken at a first point in time when the steam turbine is in a dry state, and a second digital image is taken at a later, second point in time, and the second image is compared to the first digital image to estimate moisture content of the steam flow at the second point in time.

11. The method of claim 7, wherein the at least one image sensor is positioned on a rotating component or a stationary component of the steam turbine.

12. The method of claim 7, wherein the analyzing includes analyzing each digital image to determine an intensity distribution; and the comparing includes comparing the intensity distributions for each digital image.

* * * * *